United States Patent [19]

Mendel et al.

[11] 4,138,336

[45] Feb. 6, 1979

[54] THIN LAYER CHROMATOGRAPHIC PLATES

[75] Inventors: Arthur Mendel, Vadnais Heights; Roger W. Lange, Maplewood, both of Minn.

[73] Assignee: Minnesota Mining and Manufacturing Company, St. Paul, Minn.

[21] Appl. No.: 856,655

[22] Filed: Dec. 2, 1977

[51] Int. Cl.$^2$ .............................................. B01D 15/03
[52] U.S. Cl. .................................................. 210/198 C
[58] Field of Search ........................... 210/31 C, 198 C

[56] References Cited

U.S. PATENT DOCUMENTS

| | | | |
|---|---|---|---|
| 3,301,635 | 1/1967 | Beagna et al. | 252/448 X |
| 3,340,085 | 9/1967 | Halasz et al. | 55/386 |
| 3,383,172 | 5/1968 | Biegler et al. | 252/448 X |
| 3,505,785 | 4/1970 | Kirkland | 55/67 |
| 3,600,306 | 8/1971 | Tocci | 210/31 C |
| 3,667,607 | 6/1972 | Branat | 210/198 C |
| 3,677,410 | 7/1972 | Okumura et al. | 210/198 C |
| 3,701,678 | 10/1972 | Rossler et al. | 410/198 C |
| 3,782,075 | 1/1974 | Kirkland | 55/67 |
| 3,888,972 | 6/1975 | Kiselev et al. | 423/338 |

OTHER PUBLICATIONS

Introduction to Modern Liquid Chromatography by Snyder and Kirkland, John Wiley & Sons New York, N. Y. pp. 247–254, 1974.

Porous Silica Beads — A Catalyst Support for Removal of Exhaust Gas Pollutants by Kobylinski et al., Ind. and Eng. Chem. vol. 14 No. 3, p. 147, 1975.

Corning Laboratory publication — Porous Glass Adsorbent for Thin Layer Chromatography, L975.

High Performance Liquid–Liquid Partition Chromatography on Porous Silica Microspheres by Parris, J. Chromatography Science, vol. 12, No. 12, pp. 753–757, 1974.

*Primary Examiner*—John Adee
*Attorney, Agent, or Firm*—Cruzan Alexander; Donald M. Sell; Mark A. Litman

[57] ABSTRACT

A thin layer chromatographic plate housing a substrate and bonded there to a layer of discrete, spherical inorganic metal oxide particles bonded to the substrate by an inorganic metal oxide binder the particles and binder being $SrO_2$, $TiO_2$, $ZrO_2$, or $Al_2O_3$.

10 Claims, No Drawings

THIN LAYER CHROMATOGRAPHIC PLATES

Chromatography is a process involving the analysis of materials, usually in a liquid or gaseous solution. The individual components are progressively separated from each other by the differential interaction of the respective components as they pass through a chromatographic medium. An instructive example of this process would be the passage of a solution (liquid or gaseous) through an ionic, porous medium. If the components of the solution differ in their ionic properties, their rates of passage through the medium would be different because of their different degree of interaction with the medium. With the solution allowed to pass through the medium without interruption, the solution at least partially separates into phases constituting the individual components. Whatever the nature of the interaction between components and the chromatographic medium, it is the ability to separate components which provides utility for the process.

Depending upon the efficiency of the chromatographic medium with respect to the materials being analyzed, the process may be used with widely varying degrees of sophistication. Chromatography may be used merely to determine that in fact more than one component exists or may be used to actually isolate or purify specific components. There are also different general categories of chromatographic processes in the art, such as gas-chromotography in which the mobile phase is a gas, liquid-chromatography, thin-film chromatography in which a thin film of the chromatographic medium is deposited on a sheet, reversed phase chromatography, column chromatography, etc. Each of these classes still depend upon the physical ability of a medium to separate materials in a mobile phase as they pass through the medium but require different qualities and properties in the various chromatographic uses. The present invention relates to chromatographic media which find particular utility in thin-layer chromatographic processes.

Thin layer chromatography utilizes an absorbent, usually in particulate form, which is bound to either a rigid (e.g., glass) or flexible (e.g., polyester) backing. The process of separation takes advantage of differential solubilities of components of a mixture in an eluting solvent and differential adsorption of these components on the particulate adsorbent.

The process of separation involves placing a drop of a solution of the mixture in a volatile solvent near the bottom of the plate, allowing the solvent to evaporate and then putting the edge of the plate into a reservoir of eluting solvent. As the eluting solvent migrates either up or down the plate, differential solubilities and adsorption cause components of the mixture to migrate up the plate at different rates. Thus, at the completion of the chromatography, the components of the mixture are separated into different zones or areas on the plate.

It has long been recognized that adsorbents or supports in spheroidal shape are highly desirable. Ceramic materials are materials of choice as adsorbents because of their physical and chemical properties. However, spheroidal ceramic adsorbents having optimum physical properties have not been achieved previously by those skilled in the art. For example, U.S. Pat. No. 3,340,085 discloses spherical glass beads which are overcoated by inorganic oxide particles. Such systems lack abrasion resistance and the tiny particles which act as the chromatographic medium easily are abraded away from the glass substrate.

In U.S. Pat. No. 3,383,172 hollow silica spheres are made by spray drying an aqueous slurry of a finely divided silica. The particle-to-particle interaction within the spheroid is quite low and the spheres are easily pulverized by slight abrasion. This low strength makes the particles undesirable.

In U.S. Pat. No. 3,888,972 the toughness of the ceramic spheres was improved by autoclaving a spray dried spherule derived from an aqueous suspension of silica. This autoclaving increases the bonding between particles in the spheroid by pressure and heat, but the particles produced still lack the mechanical stability of the spheres produced as described in this disclosure. These particles are then ground and sieved to produce an even size distribution. The angularity of the particles resulting from the grinding reduces the efficiency and resolution of the separation process.

Many of the producers of adsorbents for chromatography achieve mechanical stability by starting from a bulk solid which is then ground and sieved. This produces particles of heterogeneous shape and size. Such particles do not produce the separations that are achievable by virtue of having uniformly sized spheres. This lack of separation capability is related to well known surface chemical phenomena wherein sharp edges will tend to have a higher surface energy and surface charge than a smooth surface. Thus, such particles have surfaces with a graduation of surface energies which directly affect the adsorption of materials on the surface. In other words, the higher surface energy edges and corners will more tenaciously adsorb materials from solution than the remaining smoother portions of the surface. Alternatively, a non-uniform electrostatic charge on the surface may actually cause repulsion from the surface. The net result of this heterogeneous shape, then, is a poorer separation.

Many producers of thin-layer chromatographic (TLC) plates achieve mechanical stability of ground particulate adsorbents on solid substrates through the use of binders. A common binder is Plaster of Paris. Although this improves mechanical stability, the adsorbent then has a heterogeneous surface with attendant loss in surface area, decrease in separatory powers, and decrease in visualization.

The present patent discloses methods of making ceramic spherules and spherules which when used in TLC plates, produce separations superior to those known in the prior art and possess useful mechanical strength. In addition to improved separations, the resultant plates are more scratch-resistant and display better visualization. When the spherules are used in column chromatography, less resistance to flow (with attendant decrease in analytical time) results.

In the practice of this invention, the initial raw material for the ceramic microspheres is in the sol-gel state, a colloidal dispersion of metal oxide particles. Such a state is clearly a different physical state than is achieved by the simple dispersion of a silica aerogel in water. The latter easily sediments or precipitates out of solution because of its relatively larger particle size and lack of stabilizing counter ions in solution. This is in contrast with a colloidal sol where the inorganic particles in an aqueous solution usually are not visible to the naked eye. Their presence may be detected by passing a narrow beam of light through the solution and noting that the particles scatter light.

Sol particles are submicron in particle size and hence will pass through most common filter papers. Sol particles in water do not aggregate because of a stabilizing electrical charge on the surface which is termed a zeta potential. This zeta potential arises due to ionization on the surface of the particle. Depending upon the pH of the system, the fundamental particle may have a positive or negative charge. For example, in an acid media the zeta potential tends to be more positive due to protonation of silanol groups on the surface, leaving a residual charge on the solid surface. At a pH > 6, a proton is removed from the surface leaving a residual negative charge on the surface. Of course, every system in its entirety is electrically neutral, but the zeta potential arises due to a separation of electrical charges. A charge will concentrate on a solid surface while the counter ions of opposite charge are in a diffuse layer away from the solid surface. This results in a charge separation called the zeta potential which stabilizes the suspension of the dispersed sol.

Water thus plays an essential role in preventing agglomeration of particles in the sol state because it allows this separation of charges. Therefore, removal of the water removes the means for stabilization of the sol state. Once the water is removed, the sol particles interact strongly with one another through hydrogen bonding and VanderWaals forces.

There are at least two methods used in the present invention for removal of water from the ceramic sol-gel system to produce ceramic spherical particles. If one spray dries a sol, the spherical particles produced tend to be hollow. If, on the other hand, one extracts the water using alcohol, the resultant particles tend to be solid. Both solid and hollow spherical particles of the present invention derived from ceramic sols have proven efficaceous as chromatographic adsorbents.

Once the sols are condensed into spherules by spray drying, mechanical stability and activation of the surface is enhanced by a sintering process. The sintering temperature and time of sintering are critical in producing spherules with optimum physical properties. The sintering temperature will depend upon the precursor used and upon final desired properties, but is generally in the range of 500 to 900° C. The time for sintering may range from 15 minutes to five hours for the same reasons. The time duration of sintering, of course, is dependent upon equipment used, heat exchange capacity, the volume of material being processed, and the type of material. The process may be conducted in a continuous or batch process.

Once the sols are condensed into spherules by an alcohol dehydration process (as opposed to the spray dried hollow spheres), the spherules are virtually solid. Thermal treatments as low as 100° C. may be all that is necessary to remove residual organic solvents. However, for higher strength particles sintering is desirable at temperatures that do not exceed 900° C.

Where lower temperature treatments are used with the solid spheres, the starting sol should not have a surface area in excess of 200 square meters per gram so that the spheres will not exceed that surface area. It is a desirable aspect of this invention that excellent separations are achievable with support materials having this relatively low surface area.

Following the above outlined procedures one achieves physical properties for the spherules which make them ideally suited as chromatographic supports. Contrasted with prior art adsorbents which have a very high surface area, it has been discovered that performance is improved with spherules having a surface area of 2 to 200 square meters per gram. Associated with these low surface areas are pores that have a pore diameter of from 30 to 300 Å.

In some cases optimization of the physical properties of the spheres is achievable by a treatment with a one percent aqueous solution of hydrogen fluoride. For example, in one instance, through the treatment of $3Al_2O_3 \cdot B_2O_3 \cdot 2SiO_2$ spheres previously fired at 600° C., a five minute leaching with HF dropped the surface area from 400 to 150 square meters per gram and increased the pore diameter from 50 to 120 angstroms.

In addition, one may wish to slightly alter the surface properties of the ceramic spherules by either an acidic or basic treatment. For example, in the separation of negatively charged materials from a neutral species, one may desire to treat the surface of the spherules with a solution of hydrochloric acid to increase the net positive charge on the ceramic support. This would facilitate, for example, the separation of benzaldehyde from benzoic acid.

The chromatographic spheres of the present invention are made from sols of inorganic metal oxides. The metal oxides comprise $SiO_2$, $TiO_2$, $Al_2O_3$, $ZrO_2$, other metal oxides conventionally used in the formation of ceramic materials, and combinations thereof. The preferred spheres are based on silica and contain at least 25% by weight of silica. More preferred spheres have at least 60% by weight silica, and the most preferred shperes have 90 to 100% by weight silica. No matter what metal oxides are used, the process described herein for making the spheres is essentially the same. Some variation in sintering temperatures may be the most significant variation in the process to accommodate different metal oxides.

The preferred ceramic materials utilized in this invention are all silica and derivatives of silica. These include silica, alumina-boria-silica where the ingredients have a 3:1:10 mole ratio and zirconia-silica on a 1:9 mole ratio. Titania and other metal oxides may also be used in combination with silica or alone.

These other ceramic materials may also find utility as chromatographic supports if they are originally in a colloidal sol state and form spherules when either spray dried or alcohol dehydrated. Thus, spheres derived from titania, alumina and zirconia may be useful.

When spray drying the inorganic sol under conventional conditions, 85% of the resultant particles are less than a 30 micron particle size. Using smaller orifices and higher pressure, it is possible to substantially reduce the average particle size.

When making thin layer chromatoglraphic plates, the spheres are bound to a solid substrate such as glass using a binder. The conventional binder, Plaster of Paris, is generally unsatisfactory for this system as it diminishes many of the benefits of the present system. As mentioned previously, Plaster of Paris reduces the surface area of the spheres and the separations achieved with such a system are very poor. Colloidal inorganic oxides such as titania, zirconia and silica (such as Ludox ® LS from the duPont Co.) perform admirably as a binder with the ceramic spheres. They do not decrease surface area and, as they are similar to or the same as the composition of the spheres, they do not produce a system of heterogeneous surface activity.

The binder for the chromatographic spheres is also generated from sols of inorganic metal oxides. The metal oxides used as binders comprise $SiO_2$, $Al_2O_3$, $TiO_2$, $ZrO_2$, other oxides conventionally used in ceramics, and combinations thereof. Preferably the binder will have the same major constituent as does the chromatographic spheres and most preferably will have the same composition as the spheres. This most preferred embodiment provides surface properties on the thin layer chromatographic element which are uniform. The binder composition is best applied from sols having a solids content of 0.5 to 5.0% by weight, but higher solids contents may of course be used. The weight percentage of binder as compared to the total weight of binder and chromatographic spheres should be 0.5 to 60% and preferably 0.5 to 15%.

Ludox ® LS in the sol-gel state is also a preferred starting material in making these ceramic spheres. "LS" stands for low sodium content in this colloidal silica. A high sodium content may also be used as a starting material but it has been found that the preferred activating sintering temperature for these silicas has a much narrower optimum range. Therefore, the lower sodium content Ludox ® is preferred.

"Ludox ® LS" is a dispersion of colloidal $SiO_2$ in water. The silica particles have a specific surface area of 200 $m^2/g$ and an average particle diameter of about 15-16 nanometers. The dispersion has 29-32% by weight $SiO_2$, less than 0.15% by weight $Na_2O$, and is stabilized at pH 8.3.

The following examples will further describe the practice of the present invention.

EXAMPLE 1

A. Ludox ® LS colloidal silica solution was introduced into a "Nyro" spray dryer at 100 gm/min. using a 1/4J nozzle #2850 fluid cap and a #64 air cap. The air pressure was 60 psi. The inlet drying temperature was 200° C. and the outlet temperature was 100° C. Hollow spherical particles of gelled silica were produced. A portion of the particles was heated in an electric furnace at a 200° C./hr. temperature rise rate to 750° C. and held at that temperature for three hours. The particles were subsequently determined to have a surface area of 19.4 $m^2/g$ and an average pore diameter of 280 angstroms. When coated on glass plates, the particles showed excellent results as a thin layer chromatographic medium. The material, as formed, had a surface area of 172 $m^2/g$ and did not perform well as a thin layer chromatographic medium. A portion of the spray dried materials was heated to 725° C. and held at that temperature for one hour. The surface area on the fired particle was determined to be 118 $m^2/g$ and the average pore diameter was 64 angstrom units. When coated on glass plates with inorganic oxide sol binders, the materials exhibited excellent chromatographic properties and readily separated test dye mixtures. A portion of the spray dried materials was heated to 800° C. The surface area of the particles was 9.6 $m^2/g$ and the average pore diameter 151 angstrom units. When coated on glass plates with inorganic oxide sol binder (also from Ludox ® LS), the particles showed good chromatographic separation of test dye mixtures.

B. Hollow microspheres were produced in a manner similar to that described in A. The silica gel precursor used was a colloidal silica designated as Nalco 1060. The recovered particles were fired in an electric furnace to 500° C. and held at that temperature for 30 minutes. The surface area was subsequently determined to be 68.7 $m^2/g$ and the average pore diameter was 128 angstrom units. When bound on glass substrates, the particles readily separated test dye mixtures as a chromatographic medium.

C. Same as B - 650° C., 64.2 $m^2/g$ S.A.; Pore Avg. = 131 Å.

EXAMPLE 2

Solid spherical particles of silica gel were produced by adding 80 g of Ludox ® LS colloidal silica sol to 3600 ml of 2-ethylhexanol in a 4 liter beaker being stirred at 6000-6400 rpm by a high speed mixer. The mixture was stirred for seven minutes to extract the water from the silica sol and to form solid spheres. The silica gel beads thus formed were recovered by filtration. The particles were solid, transparent and ranged in size from 2-40 microns. The particles were then heated in an electric furnace to 500° C. and held at that temperature for one hour and 40 minutes. Subsequent testing showed the particles to have a surface area of 148 $m^2/g$ and an average pore diameter of 57 angstrom units. Separation of test dyes on glass plates coated with the microspheres was only fair with this surface area and pore diameter.

EXAMPLE 3

Ten grams of silica microspheres (as per Example 1A), were thoroughly mixed with one gram $CaSO_4$ (Plaster of Paris — a conventional binder), and 100 mg of mixed Zn and CdS (an inorganic phosphor) and 13 milliliters of water. After mixing, the mixture was coated on a glass microscope slide. This was accomplished by placing the slurry in a chamber of a knife coater, dripping the slurry onto the glass plates and passing the plates underneath the knife wherein the thickness of the coating is sheared to 250 $\mu$ or approximately 10 mils. The glass slide was air dried at room temperature overnight.

By thin layer chromatography using the above prepared slide, test separations were conducted with a commercially available dye mixture consisting of indophenol, Sudan Red and methyl yellow. Benzene was used as the developing liquid and the three separated dyes were easily visualized. However, adhesion of the silica microspheres to the glass slides wherein Plaster of Paris was used as a binder was very poor. This was evidenced by the fact that when the slide was handled, the particles slipped off.

EXAMPLE 4

A mixture of 10 grams silica microspheres as per Example 1 were mixed with approximately 15 milliliters water and 0.1, 0.3, 0.5, 1.0 and 1.5 grams solids respectively of Ludox ® LS (a silica sol, 30% in water, low sodium content, available from the E. I. duPont Company, which is used here as a binder). Each slurry was knife coated onto glass microscope slides and air dried at room temperature overnight.

Using the commercial dye mixtures of Example 3, benzene as the developing liquid and the plates prepared above, excellent dye separations were observed visually and when the slides were handled, the microspheres adhered tenaciously to the glass surface.

EXAMPLE 5

To illustrate the superior scratch resistance and adhesiveness of this new system, glass plates as prepared in Example 4 along with commercially available plates were compared in the following tests.

Using a weighted stylus with a ball point pen tip, the sytlus was slowly moved over the uncoated glass surface impinging upon the coated area of the slide. The weight at which the stylus disrupts the coating was recorded.

| | |
|---|---|
| Silica microspheres of Example 4 | >200 grams |
| E. Merck TLC (Glass) | 65 |
| E. Merck TLC (Polyester) | 30 |
| Woelm Co. "Rapid Plate" | 55 |
| Quantam Ind. LQ6F (Glass) | 90 |
| Quantam Ind. Q4F (CaSO$_4$ binder-glass) | 15 |
| Analtech, GF/MH (medium hard) | 75 |
| Analtech, HLF (hard plate glass) | 100 |

A second test gave relative readings relating to the over all layer hardness and scratch resistance of the various thin layer chromatography plates.

In this test a twin stylus with a small hardened steel tip was placed on the surface of the plate.

The first weight recorded was the weight on the stylus wherein as the stylus moved over the coating at a constant rate, first incidence of a scratch in the coating was evident. The second reading coincides with the force necessary for the stylus tip to penetrate the coating to the substrate.

| | Gms. to Scratch | Gms. to Penetrate |
|---|---|---|
| 3M silica microspheres-Ludox ® binder | 140 | >460 |
| E. Merck TLC (Glass) | 55 | 100 |
| E. Merck TLC (Polyester) | 50 | 165 |
| Woelm Co. "Rapid Plate" | 50 | 160 |
| Quantum Ind. LQ6F (Glass) | 50 | 270 |
| Quantum Ind. Q4F (Glass) | 17 | 21 |
| Analtech GF/MH | 30 | 160 |
| Analtech HLF | 50 | 170 |

The superiority of the system utilizing silica microspheres and inorganic oxide sols as a binder is clearly evident.

EXAMPLE 6

A batch of silica microspheres was made as per Example 1. The spheres were fired at 750° C. for three hours. The resultant particles had a surface area of 19.4 square meters per gram and an average pore diameter of 230 A. Spheres were coated and bound to glass slides using 1% Ludox® LS as the binder, the percentage weight being based on total solids in the coating.

Thin layer chromatographic separations of o-, m-, and p-nitroaniline were conducted using a developing liquid consisting of a mixture of chloroform, heptane and n-butanol in a 25:24:1 ratio by volume. Excellent separations were achieved wherein $R_f$ values of 0.48, 0.42 and 0.35 were achieved for the o-, m-, and p-nitroanilines respectively.

EXAMPLE 7

Solid spherical particles of titania were produced by adding 80 grams of colloidal titania sol to 3600 ml of 2 as in Example 2. The sol had 30% solids content of titania, which after extraction were solid particles of from 2-50 microns in diameter. The particles were sintered with the following results.

| Temperature | Time | Surface Area |
|---|---|---|
| 200° C. | 1 hr | 107 m$^2$/g |
| 310° C. | 2 hr | 133 m$^2$/g |
| 370° C. | 2 hr | 68.6 m$^2$/g |
| 500° C. | 2 hr | Pore Size 20–100 A |

It was found that the titania spheres fired at about 310° C. had the highest surface area and exhibited the best chromatographic separation when coated out with an inorganic oxide binder into a thin layer chromatographic plate.

What is claimed is:

1. A thin layer chromatographic plate comprising a substrate and bonded thereto a layer of discrete, spherical inorganic metal oxide ceramic chromatographic particles having a surface area of 2 to 200 square meters per gram and pore diameters of 30 to 300 A, said particles being bonded to said substrate by an inorganic metal oxide binder.

2. The plate of claim 1 wherein the binder comprises 0.5 to 60% by weight of the total weight of binder and particles.

3. The plate of claim 1 wherein the substrate is rigid.

4. The plate of claim 1 wherein the metal oxide chromatographic particles comprise SiO$_2$, TiO$_2$, ZrO$_2$, or Al$_2$O$_3$.

5. The plate of claim 4 wherein the metal oxide binder comprises SiO$_2$, TiO$_2$, ZrO$_2$, or Al$_2$O$_3$.

6. The plate of claim 1 wherein the metal oxide chromatographic particles comprise at least 25% by weight silica.

7. The plate of claim 1 wherein the metal oxide chromatographic particles comprise at least 60% by weight of silica and the metal oxide binder comprises at least 60% by weight of silica, said binder being present in 0.5 to 60 weight percent of the total weight of binder and chromatographic particles.

8. The plate of claim 1 wherein the metal oxide chromatographic particles comprise at least 90% by weight silica and the binder comprises at least 90% by weight of silica.

9. The plate of claim 1 wherein the metal oxide chromatographic particles are hollow.

10. The plate of claim 1 wherein the metal oxide chromatographic particles are solid.

* * * * *